United States Patent [19]

Jordan

[11] 4,446,126

[45] May 1, 1984

[54] ANTITHROMBIN-HEPARIN COMPLEX AND METHOD FOR ITS PRODUCTION

[75] Inventor: Robert E. Jordan, Concord, Calif.

[73] Assignee: Cutter Laboratories, Inc., Berkeley, Calif.

[21] Appl. No.: 357,504

[22] Filed: Mar. 12, 1982

Related U.S. Application Data

[63] Continuation of Ser. No. 192,170, Sep. 30, 1980, abandoned.

[51] Int. Cl.³ .................... A61Y 31/725; A61Y 35/14
[52] U.S. Cl. .................................... 424/183; 424/101
[58] Field of Search .............................. 424/101, 183

[56] References Cited

PUBLICATIONS

Jordan et al, J. Biol. Chem. 254, 8, pp. 2902–2913, 4/25/79.
Rosenberg et al., Proc. Nat. Acad. Sci., (1978), 75:7, 3065–3069.
Rosenberg et al., BBRL (1979), 86:4, 1319–1324.

*Primary Examiner*—Stanley J. Friedman
*Attorney, Agent, or Firm*—Theodore J. Leitereg; David J. Aston; Lester E. Johnson

[57] ABSTRACT

A complex of antithrombin and high activity heparin is provided for use as a potent anticoagulant for humans. The complex is prepared by reversibly immobilizing it on a lectin-containing, water-insoluble gel matrix and then removing it from the matrix.

21 Claims, No Drawings

ANTITHROMBIN-HEPARIN COMPLEX AND METHOD FOR ITS PRODUCTION

This application is a continutation of application Ser. No. 192,170, filed Sept. 30, 1980, now abandoned.

BACKGROUND OF THE INVENTION

1. Field of the Invention:

This invention relates to and has among its objects the provision of a novel anticoagulant for human use. It is a particular object of the invention to prepare an antithrombin-high activity heparin complex in large quantities using a novel lectin-containing, water-insoluble gel matrix to which antithrombin and heparin are applied. Further objects of the invention will be evident from the following description wherein parts and percentages are by weight unless specified otherwise.

2. Description of the Prior Art:

Heparin is a glycosaminoglycan, having uronic acid, glucosamine, and sulfate moieties, that functions as a blood anticoagulant by binding to the inhibitor antithrombin and accelerating the rate at which this inhibitor neutralizes serine proteases of the coagulation mechanism.

The injection of unfractionated heparin alone (either intravenously or subcutaneously) is routinely employed for the treatment of thromboembolism or for the prevention of clot formation in at-risk patients. Despite its widespread and growing use for these purposes, problems concerning side effects and efficacy have been pointed out. Some of the problems associated with current anticoagulant therapy are the following:

(1) Patients often demonstrate widely different dose responses to administered heparin. This requires a rather individualized treatment procedure and constant monitoring of the resulting clotting characteristics. Quite often, the desired dosage is exceeded which necessitates the neutralization of the excess heparin.

(2) Heparin, as it is used clinically, is approximately 30% active as an anticoagulant (as defined by its ability to interact with antithrombin which results in the rapid inhibition of thrombin and other coagulation proteases). The majority of administered heparin (70%) shows no particular affinity for antithrombin but can interact with many other plasma proteins with consequences that may be undesirable. The best example of this phenomenon is the activation of lipoprotein lipase which results in the clearance of circulating triglyceride.

(3) Heparin is a highly charged polyanion and is capable of many non-specific electrostatic interactions with plasma proteins, blood cells, and endothelial surfaces. Upon injection heparin becomes distributed among these components. Although antithrombin binds in a specific fashion and with high affinity to the active fraction of the total heparin, is is unlikely that all of the anticoagulant heparin binds to the plasma antithrombin. Thus, the actual anticoagulant dosage of heparin received during heparin therapy is a complex function of any number of equilibria which reduce the amount of productive heparin-antithrombin complexes formed.

(4) Heparin has been implicated as a cause of thrombocytopenia due to its interaction with platelets in patients undergoing prolonged anticoagulant therapy.

(5) Circulating antithrombin levels have been shown to decrease as a result of prolonged administration of heparin. Antithrombin levels lowered in this way are reported to remain depressed for several days following the end of treatment. This may be a particularly undesirable effect in patients predisposed to thrombosis.

(6) In patients with congenital antithrombin deficiency, the administration of heparin may not be completely efficacious.

The administration of antithrombin as also been proposed to be a means of controlling undesirable clot-formation in at-risk patients. Those who might benefit most from this therapy would be those congenitally deficient in antithrombin as well as individuals undergoing certain types of surgery. In order for this type of therapy to be effective, however, very large amounts of antithrombin would be required. Also, treatment of congenital antithrombin deficients with antithrombin concentrates would require large amounts of this protein at frequent dosages since the plasma half-life of antithrombin is about three days.

Fractionation of heparin into high and low activity components is difficult because heparin species possessing active chain sequences are virtually indistinguishable from those possessing inactive chains. However, heparin has been separated into high activity and low activity components by sucrose density gradient centrifugation of heparin mixed with antithrombin-heparin cofactor (Lam et al, *Biochemical and Biophysical Research Communications*, 1976, Vol. 69, No. 2, pages 570–577). Heparin also has been fractionated by affinity chromatography on immobilized antithrombin (Höök et al, *FEBS Letters*, 1976, Vol. 66, pages 90–93). In this method antithrombin is coupled covalently with a cyanogen bromide-activated, water-insoluble matrix, such as, for example, Sephadex ®, Sepharose ®, etc. Heparin is applied to the immobilized antithrombin material, which adsorbs the high-activity heparin species. After separation of the matrix containing the adsorbed high activity component from the low activity heparin component, the matrix is treated with a high salt medium to elute the high activity heparin species therefrom.

An alternative method involves the separation of heparin-antithrombin complexes from unbound heparin by gel chromatography on Sephadex ® G100. However, due to the size heterogeneity inherent in commercial heparin preparations and the resultingly broad chromatographic profile of the heparin itself, the above method must employ heparin fractions of defined molecular weight in order to permit the separation of the heparin-antithrombin complex. This has been accomplished with a low molecular weight heparin species having an average molecular weight of 6000 daltons (Rosenberg et al, *Proc. Nat. Acad. Sci.*, 1978, Vol. 75, No. 7, pages 3065–3069). In this case, a heparin-antithrombin complex was separated from free heparin in an initial gel chromatographic step and was subjected to a second chromatography in the presence of high salt to disrupt the complex. The high affinity heparin obtained in this sequence had a specific anticoagulant activity of about 360 units/mg compared to the starting pool of 96 units/mg. A low affinity heparin pool of 4 units/mg was also obtained by repetitive depletion of the starting material.

A complex of antithrombin and high molecular weight, high affinity heparin was also prepared by gel chromatography on Sephadex ® G100 (Rosenberg et al, *B.B.R.C.*, 1979, Vol. 86, No. 4, pages 1319-1324). In this instance, the complex was separated from excess antithrombin for the purpose of analytical characterization of the ratios contained and required the use of a heparin species previously fractionated both for size and activity.

One major problem confronting the industry in all of the above-described methods is that the fractionation or preparation has been accomplished only on a laboratory scale. In other words, large scale manufacture or manufacture of pharmaceutically useful amounts has not been realized either because of limitations inherent in the method or because of the limited availability of antithrombin. Compositions comprising a complex of antithrombin and high activity heparin in a pharmaceutically useful amount, essentially free of low activity heparin, the molecular weight of the high activity heparin being representative of non-fractionated-by-size heparin, have not been obtained in the prior methods.

Fractionation of heparin into high and low activity components is complicated further by the fact that antithrombin coupled to a water-insoluble matrix cannot be recovered without substantial or total destruction of the antithrombin. This results because the antithrombin is covalently bound to the matrix by means of, for example, a cyanogen bromide coupling process, and the conditions necessary to cleave the coupling destroy the antithrombin.

Recently, a new method for the measurement of the binding of ligands to solubilized membrane receptors, such as a receptor for epidermal growth factor-urogastrone (EGF-URO) was described by Nexo et al, *J. Biol. Chem.*, 1979, Vol. 254, No. 18, pages 8740-8743. The soluble receptor is first immobilized on lectin-agarose beads and ligand binding is then determined on the bead-bound receptor. The chromatographic and binding properties of solubilized receptor can be studied due to the restoration of the ligand recognition property of the receptor. After the solubilized receptor is immobilized on lectin agarose, the binding of a ligand, such as EGF-URO, to the immobilized receptor is rapid, reversible, peptide specific, and of high affinity. The author notes that his method deserves consideration for the study of any receptor that recognizes a ligand free of carbohydrate.

SUMMARY OF THE INVENTION

I have found that a complex of antithrombin and high activity heparin can be prepared by reversibly immobilizing the complex on a lectin-containing, water-insoluble matrix. The antithrombin first becomes reversibly bound to the matrix to which the high activity component of heparin next becomes bound. The low activity or unbound heparin may be separated selectively from the matrix which then can be treated further to give the aforementioned complex. The antithrombin and heparin can be applied to the matrix as a mixture, or the antithrombin can be applied first followed by the heparin. The so-prepared antithrombin-high activity heparin complex is suitable for human use as an anticoagulant. It is to be noted that use of any antithrombin-heparin complex as a therapeutic agent, such as, for example, an anticoagulant, heretofore, has been unknown in the art.

A primary advantage of the invention is that an antithrombin-heparin complex can be prepared for therapeutic use in large quantities by a quick and simple procedure. Thus, a valuable therapeutic agent is now available in pharmaceutically useful amounts; such an agent and its use are unknown in the prior art. The antithrombin-heparin complex of the invention is a highly potent therapeutic agent because the instant complex contains only the high activity component of heparin. Prior to elution of the antithrombin high activity heparin species from the matrix, the low activity heparin species is removed.

DESCRIPTION OF THE PREFERRED EMBODIMENTS

In the following description emphasis is directed to the preparation of an antithrombin-HAH complex. Lectin-containing, water-insoluble matrix is prepared from a water-insoluble polymeric material and a lectin. As the water-insoluble polymeric material one may use any material to which the lectin can be bound; thus, one may use, by way of example and not limitation, certain cross-linked dextrans, cross-linked agarose, etc. For instance, one may employ Agarose or Sepharose ® 4B, or the like. The lectin is covalently bound to the matrix by means of cyanogen bromide or the like, using the method described by Cuatrecasas, *J. Biol. Chem.*, 1970, Vol. 245, pages 3059-3065. It should be noted that any method that covalently attaches a lectin to an insoluble matrix could be used to prepare the matrix of this invention.

Lectins are carbohydrate-binding proteins of nonimmune origin that agglutinate cells and/or precipitate complex carbohydrates and are isolated usually from seeds of plants. The preferred lectin for preparing the matrix for fractionating heparin is Concanavalin A. However, other D-mannose (D-glucose)-binding lectins may be used such as, for example, those described by Goldstein et al, in *Advances in Carbohydrate Chemistry and Biochemistry*, 1978, Vol. 35, pages 334-335.

The lectin-containing, water-insoluble matrix is mixed with antithrombin which becomes reversibly bound to the matrix, particularly to the lectin on the matrix. In a preliminary step, which is optional although preferred, the lectin-containing, water-insoluble matrix is equilibrated in an appropriate buffer generally characterized as the same buffer solution as that used hereinafter in which a mixture of antithrombin and heparin is applied to the matrix. This buffer contains sodium chloride at a level no greater than 0.25 M, preferably at physiological concentration (0.15 M), and has a pH in the range of 6 to 8.5. The equilibration is carried out for a period of about 0.1-2 hours at a temperature of about 5-30° C.

After the lectin-containing, water-insoluble matrix is equilibrated, it is mixed with antithrombin, either pure or a mixture with other proteins that will not bind to the lectin, together with an excess of heparin, in an amount such that the resultant system will contain high activity heparin (HAH). Usually, about 50-1000 parts of matrix are mixed with one part of antithrombin. By an excess of heparin is meant that about 1-100 parts, preferably 4-20 parts, of unfractionated heparin are employed per part of antithrombin.

The mixture of antithrombin, heparin, and the lectin-containing water-insoluble matrix is held in contact for a period of time and at a temperature sufficient to allow the antithrombin to bind to the lectin portion of the matrix. During that time the HAH becomes complexed to the antithrombin. Thus, the mixture of antithrombin, heparin, and the matrix are held for a period of about 0.1-2 hours at a temperature compatible with the system, usually at a temperature of about 5-30° C. Generally, the antithrombin and heparin are in solution in an appropriate buffer, preferably, the buffering system employed in the above-described equilibration of the lectin-containing, water-insoluble matrix; and the solution is applied to a bed or column of the lectin-containing matrix.

Next, the matrix is washed to remove unbound heparin. The wash solution should contain a physiologically acceptable salt having an ionic strength sufficient to remove all unbound heparin from the matrix but insufficient to remove the antithrombin-HAH complex, preferably an ionic strength of about 0.1-0.4. The pH of the wash solution should be about 6.0-8.5.

A suitable aqueous solution in accordance with this aspect of the invention is, by way of example and not limitation, 0.1-0.4 M sodium chloride (ionic strength=0.1-0.4) at pH 6.0-8.5. Ionic strengths less than 0.1 should be avoided. Low ionic strength promotes non-specific interactions between the lectin and heparin itself. Low temperatures are to be avoided since such temperatures also promote the above interactions. Thus, the preparation of the complex should be conducted at a temperature greater than 5° C., preferably within the temperature range 20°-30° C., and no greater than 37° C. In general, the temperature and ionic strength should be adjusted to achieve the appropriate binding needed for selective complex formation where higher temperatures require lower ionic strengths within the above ranges.

In general, the matrix is washed until no unbound heparin appears in the wash solution as determined by known methods.

The matrix, having been stripped of unbound heparin as described above, may be treated to separate an antithrombin-HAH complex by contacting the matrix with a solution of a carbohydrate having the ability to displace the complex from the matrix. The concentration of carbohydrate in the solution and the pH of the solution should be sufficient to cause separation of the complex from the matrix. Generally, about 0.02-0.5 M aqueous solution of carbohydrate at pH 6-8.5 is applied until the antithrombin is removed from the matrix. As the carbohydrate one may use those carbohydrates disclosed by Goldstein et al, supra, such as glucopyranosides, mannopyranosides, and fructofuranosides. Mono- and disaccharides also may be employed to separate the complex from the matrix and are preferred in this particular step. Thus, one may use, by way of example and not limitation, glucose, maltose, mannose, galactose, fructose, lactose, sucrose, and the like. It is within the compass of the invention to employ sugar alcohols such as mannitol, sorbitol, and the like to isolate the aforementioned complex.

After separation of the complex, the eluted solution may be treated to reduce its carbohydrate concentration by conventional means such as by dialysis, diafiltration, etc., and then processed to put it into condition for use. Generally, the eluate is concentrated also, that is, treated to reduce its water content, by methods known in the art for removing water from biologically active proteins without reducing substantially their biological activity. The concentrates may be sterilized by conventional means, sterile-filtered, and treated to render them non-hepatitis infective.

Antithrombin-HAH complex concentrates can be formulated into pharmaceutical preparations. The term "pharmaceutical preparation" is intended in a broad sense herein to include preparations used for therapeutic purposes, for reagent purposes, for diagnostic purposes, for tissue culture purposes, and so forth. The pharmaceutical preparation intended for therapeutic use should contain a therapeutic amount of the complex, i.e., that amount necessary for preventative or curative health measures. If the pharmaceutical preparation is to be employed as a reagent, then it should contain reagent amounts of complex. Similarly, when used in tissue culture or as a culture medium the pharmaceutical preparation should contain an amount of complex sufficient to obtain the desired growth. It is a characteristic of compositions comprising the antithrombin-HAH complex prepared in accordance with the present invention that they contain the complex in pharmaceutically useful amounts. As mentioned earlier, an antithrombin-heparin complex has been prepared only as an intermediate in the laboratory scale production of heparin by gel chromatography; consequently, compositions containing the complex in pharmaceutically useful amounts have, heretofore, been unknown. Furthermore, in the above heparin preparation using gel chromatography, the heparin necessarily had to be fractionated by size prior to use; and only fractionated-by weight heparin was employed. The molecular weight of the high activity heparin in the present complex is representative of non-fractionated-by-size heparin, i.e., derived from heparin not previously fractionated by size. It is also noteworthy that the instant complex is essentially free of low activity heparin, and the activity of the high activity heparin in the complex is greater than about 300 U/mg, usually within the range of about 400-750 U/mg.

To prepare them for intravenous administration the compositions are constituted usually in water containing physiologically compatible substances such as sodium chloride, glycine, sugar and the like in physiologically compatible concentrations and having a buffered pH compatible with physiological conditions. Generally, guidelines for intravenously administered compositions are established by governmental regulations.

Since many of the problems and limitations of current heparin therapy appear to result from inadequate levels of formed complexes with circulating antithrombin, the administration of a preformed HAH-antithrombin complex solves this problem. Thus, the levels of HAH-antithrombin complex obtained would not be subject to the conditions of the many equilibria which normally would prevent the full anticoagulant expression of heparin administered alone. Further, since no additional heparin would be given other than that bound to the antithrombin, it is to be expected that side effects resulting from the interaction of heparin with other serum components would be greatly diminished. Also, in addition to the increased potency and resulting lowered dosage of heparin required, the dose response characteristics of the HAH-antithrombin administration are expected to be much more predictable than with current methods.

Two other advantages apply. First, circulating antithrombin levels should not be decreased as a result of this anticoagulant therapy since, presumably, only exogenously added antithrombin should be complexed with HAH and thus subject to rapid clearing (heparin has a circulating half-life of only 90 minutes). Second, administration of antithrombin complexed with HAH should be beneficial to congenital antithrombin deficients for whom complete restoration to normal circulating levels may be economically difficult, and the administration of heparin alone is ineffective.

It is also within the scope of the invention to initially reversibly immobilize, in the absence of heparin, antithrombin on the equilibrated lectin-containing, water-insoluble matrix from above and use the resulting matrix to prepare the complex. Thus, the matrix may be mixed with antithrombin, either pure or in a mixture of other proteins that will not bind to the lectin on the matrix, in an amount such that the resulting system will produce an antithrombinHAH complex. About 50–1000 parts of matrix are mixed usually with one part of antithrombin. The reaction conditions for binding antithrombin to the matrix are the same as those described above when heparin is present.

In situations where the antithrombin solution (in an appropriate buffer system as described above) is not applied to a bed or column of matrix, the matrix with bound antithrombin is treated to separate it from the antithrombin solution. This may be accomplished by techniques known in the art such as filtration, decantation, and the like.

Next, the matrix is washed to remove residual antithrombin solution and impurities not bound to the matrix. Preferably, the wash solution is the same buffer solution described above in the equilibration step.

It is characteristic of the aforedescribed system that the antithrombin is bound reversibly thereto through the lectin on the matrix. The antithrombin is bound sufficiently to immobilize it but not great enough to cause the destruction of antithrombin upon its removal from the matrix. Thus, the antithrombin is non-destructively-removably bound to the lectin-containing matrix. The exact nature of this reversible binding is not known. However, hydrogen bonding and chargedipole interactions may be involved.

In the next step in this particular embodiment of the invention, heparin is contacted with the antithrombin-containing, lectin-containing, water-insoluble matrix onto which the high activity heparin (HAH) is adsorbed. In general practice the unfractionated heparin is in the form of a solution in a buffer system containing sodium chloride in a concentration less than 0.4 M, usually about 0.1–0.4 M, and preferably at physiological concentration, i.e., 0.15 M. The pH of the buffer solution should be about 6.0–8.5, usually about 7.5. As the buffer solution one may use, for example, a mixture of 0.01 M TRIS (hydroxymethyl) aminomethane (TRIS) and 0.15 M sodium chloride. The amount of heparin mixed with the matrix should be sufficient to maximize the activity of HAH obtained in the complex, no less than about 1 part, preferably 4–20 parts, of unfractionated heparin per part of antithrombin on the matrix is applied to the matrix. The heparin may be in pure form or it may be mixed with other proteins and the like which do not bind to antithrombin in significant amounts. Generally, contact between the heparin solution and the matrix is achieved by forming a bed of freshly equilibrated matrix and passing the heparin solution therethrough.

By the foregoing it is not meant to limit the invention to a particular method of preparing the antithrombin-heparin complex of the invention. I have discovered a novel therapeutic agent, namely, an antithrombin-heparin complex and have developed also a novel method for its production. Antithrombin-heparin complexes for anticoagulant use obtained by other methods are within the scope of my invention. Furthermore, previously fractionated heparin can also be used in my method.

EXAMPLES

The invention is demonstrated further by the following illustrative examples.

Assay Methods

Antithrombin III. The Lowry protein assay was used using human serum albumin as the standard (Lowry et al, *J. Biol. Chem.*, 1951, Vol. 193, pages 165–275).

Heparin. Two assays were employed
  (a) Carbazole Assay: A quantitative assay for heparin based on a standard curve of uronic acid. A uronic acid content of 30% was assumed for heparin (Hook et al, *FEBS Letters*, 1976, Vol. 66, pages 90–93). The assay was described by Bitter et al, in *Anal. Biochemistry*, 1962, Vol. 4, pages 330–334.
  (b) Azure A Method: A qualitative assay based on the method of Jacques et al, *J. Physiol.* (London), 1949, Vol. 109, pages 41–48, (see also Lam et al, *BBRC*, 1976, Vol. 69, pages 570–577).

Anticoagulant Activity of Heparin. The activity of all heparin fractions was related to that of commercially obtained preparation (Lipo-Hepin ®, Riker Laboratories, Inc.) whose U.S.P. unitage was defined on the label. A standard curve was established with the above heparin, and all heparin fractions of unknown activity were determined by comparison to this curve by the following scheme:
  (1) A 200 µl sample containing antithrombin (approximately 30 µg/ml) and 200 µl of a heparin-containing solution were combined and warmed to 37°.
  (2) A 200 µl sample of a solution containing thrombin (Pentex ® bovine thrombin, Miles Laboratories, Inc.) at a level in excess of the antithrombin was added to the mixture of (1) above and rapidly mixed.
  (3) After exactly 30 seconds, 200 µl of a solution of 1 mM S-2238 (H-D-Phe-L-Pip-L-arg-p-nitroanilide, Kabi Diagnostica, Sweden) and 0.5 mg Polybrene ® (Aldrich Chemical Co., Inc.) was added to the mixture which was again rapidly mixed.
  (4) After exactly 60 seconds, 200 µl of 50% acetic acid was added to stop the esterolytic reaction.
  (5) The U.V. absorbance of each sample was determined at 405 nanometers (nm).

EXAMPLE 1

Preparation of Antithrombin-Concanavalin A-Sepharose Support

A column (1.6×5 cm) was prepared from a 10 ml suspension of Concanavalin A-Sepharose (Pharmacia Corp., Piscataway, N.J.). This agarose gel contains 8 mg of the lectin protein covalently bound per ml of swollen gel as stated by the manufacturer. The column was equilibrated with a buffer containing 0.15 M NaCl and 0.01 M TRIS, pH 7.5. (Optionally, this buffer solution can include agents to prevent bacterial growth, e.g., sodium azide 0.02% and other salts which stabilize Concanavalin A, namely, 0.1 mM calcium chloride and 0.1 mM manganese chloride, which are not otherwise essential for the experiments to be described).

A solution containing antithrombin (0.83 mg/ml) in the above buffer was applied to the column. Protein which was not bound to the column was monitored by ultraviolet (UV) spectioscopy at 280 nm. An unbound protein fraction was found to contain 1.13 mg which represents approximately 9% of the applied material (12.5 mg). Thus, approximately 11.4 mg of antithrombin was bound by the Concanavalin A-Sepharose, which is approximately 1.4 mg antithrombin per mg of Concanavalin A lectin.

EXAMPLE 2

Preparation of Antithrombin-HAH Complex

Heparin (85 mg) from Sigma Chemical Co., (St. Louis, Missouri) was dissolved in 10 ml of an aqueous solution containing 0.15 M NaCl and 0.01 M TRIS, pH 7.5, and the solution was applied to a column prepared as in Example 1. The column was then eluted with an aqueous buffer containing 0.01 M TRIS, pH 7.5, and 0.15 M NaCl until no further heparin was detected in the eluate. The presence of heparin in column eluates was monitored by a modification of the Azure A Method in which the presence of the mucopolysaccharide results in an increase in the visible absorption of the dye at 500 nm.

Next, the column was eluted with a neutral sugar dissolved in the above buffer. In this case, a solution of 0.2 M 1-0-methyl-α-D-glucopyranoside was employed. The elution of antithrombin-HAH from the column was detected by UV absorption at 280 nm and the Azure A Method described above.

The heparin contained in the above complex was shown to have high activity, exhibiting a specific anticoagulant activity of 500 units/mg. Quantitation of the relative amounts of material contained in the complex indicate that there is a molar excess of antithrombin to heparin that is approximately two-fold. This value is expected to vary between 1 to about 2.5 given the heterogeneous size distribution of heparin and the ability of the larger species to interact with more than one antithrombin molecule.

I claim:

1. A method for preparing a composition having as its sole effective anticoagulant agent an antithrombin-heparin complex, comprising the steps of:
    (a) reversibly binding antithrombin to a lectin-containing water-insoluble matrix;
    (b) contacting said matrix and said antithrombin bound thereto with heparin, whereby an active portion of said heparin complexes with said antithrombin;
    (c) washing said matrix to remove portions of heparin not complexed to said antithrombin;
    (d) displacing said antithrombin-heparin complex from said matrix; and
    (e) thereby recovering said antithrombin-heparin complex substantially free from uncomplexed antithrombin and uncomplexed heparin.

2. The method of claim 1 wherein the lectin is Concanavalin A.

3. The method of claim 1 wherein the water-insoluble matrix is an agarose gel.

4. The method of claim 1 wherein the unbound heparin is separated from the matrix by treating the matrix with an aqueous salt solution having an ionic strength sufficient to remove unbound heparin but insufficient to remove high activity heparin from the matrix.

5. The method of claim 1 wherein the matrix is contacted with an aqueous carbohydrate solution, the carbohydrate being present in an amount sufficient to separate the reversibly bound complex from the matrix.

6. The method of claim 5 wherein the carbohydrate is a monosaccharide.

7. The method of claim 6 wherein the carbohydrate is selected from the group consisting of glucose, mannose, galactose, and fructose.

8. The method of claim 5 wherein the carbohydrate is a dissacharide.

9. The method of claim 8 wherein the carbohydrate is selected from the group consisting of maltose, sucrose, and lactose.

10. A method of preparing a complex of antithrombin and high activity heparin, which comprises
    (a) contacting a lectin-containing, water-insoluble matrix with antithrombin and heparin for a period of time and at a temperature sufficient to allow the antithrombin to bind reversibly to the lectin portion of the matrix and the high activity heparin component of the heparin to complex with the antithrombin,
    (b) washing the matrix with a solution having an ionic strength sufficient to remove unbound heparin from the matrix but insufficient to remove the antithrombin-high activity heparin complex therefrom,
    (c) contacting the matrix with a solution of a carbohydrate having the ability to displace the complex from the matrix and
    (d) recovering said complex substantially free of uncomplexed antithrombin and uncomplexed heparin.

11. The method of claim 10 wherein 50–100 parts of matrix are contacted in Step (a) with one part of antithrombin on a weight basis.

12. The method of claim 10 wherein 1–100 parts of heparin per part of antithrombin on a weight basis are contacted with the matrix in Step (a).

13. The method of claim 10 wherein the matrix prior to contact with antithrombin and heparin is equilibrated with a buffer solution containing no greater than 0.25 M sodium chloride and having a pH of about 6–8.5.

14. The method of claim 10 wherein the wash solution of Step (b) has an ionic strength of about 0.1–0.4 and a pH of about 6–8.5.

15. The method of claim 10 wherein the temperature in Step (a) is greater than 5° C. but no greater than 37° C.

16. The method of claim 10 wherein the time of contact in Step (a) is about 0.1–2 hours.

17. The method of claim 10 wherein the matrix is contacted with a solution in Step (c) containing 0.02–0.5 M carbohydrate and having a pH of about 6–8.5.

18. The method of claim 10 wherein the carbohydrate is selected from the group consisting of glucopyranosides, mannopyranosides, fructofuranosides, monosaccharides, dissacharides, and sugar alcohols.

19. The method of claim 10 which further includes the step of reducing the carbohydrate concentration of the complex displaced from the matrix in Step (c).

20. The method of claim 10 wherein the lectincontaining, water-insoluble matrix in Step (a) is formed by covalently attaching a lectin to a water-insoluble matrix.

21. A pharmaceutical preparation as an anticoagulant comprising a complex of antithrombin and high activity heparin prepared by the method of claim 10 wherein the activity of the high activity heparin in the complex is greater than about 300 Units per milligram and wherein the high activity heparin in the complex is derived from heparin not previously fractioned by size.

* * * * *